United States Patent [19]

Combourieu et al.

[11] Patent Number: 4,762,834
[45] Date of Patent: Aug. 9, 1988

[54] 3-ALKOXY-2-(N-PYRROLIDINO)-N-PYRIMIDINYL- OR -N-PYRAZINOLPROPYLAMINES USEFUL FOR TREATMENT OF CARDIOVASCULAR DISORDERS

[75] Inventors: Michel Combourieu, Aurillac; Jacques A. L. Simond, Les-Martres-de-Veyre; André J. C. Monteil, Chatel-Guyon, all of France

[73] Assignee: Riom Laboratoires C.E.R.M. "Rl-Cerm", S.A., Riom, France

[21] Appl. No.: 898,834

[22] Filed: Aug. 20, 1986

Related U.S. Application Data

[63] Continuation of Ser. No. 688,424, Jan. 2, 1985, abandoned.

[30] Foreign Application Priority Data

Jan. 18, 1984 [FR] France .................. 84 00757

[51] Int. Cl.⁴ ................ A61K 31/495; A61K 31/505; C07D 403/12; C07D 403/14
[52] U.S. Cl. .................... 514/252; 514/275; 544/331; 544/332; 544/336; 544/405
[58] Field of Search ............ 544/332, 322, 328, 331, 544/405, 336; 514/252, 256, 275

[56] References Cited

FOREIGN PATENT DOCUMENTS 1595031 8/1981 United Kingdom .

OTHER PUBLICATIONS

Alfred Burger, *Medicinal Chemistry*, Third Edition, Part I, Wily–Interscience, 1970, pp. 74–77.

Primary Examiner—Robert Gersil
Assistant Examiner—Cecilia Shen
Attorney, Agent, or Firm—Wegner & Bretschneider

[57] ABSTRACT

The present invention relates to new compounds of the general formula:

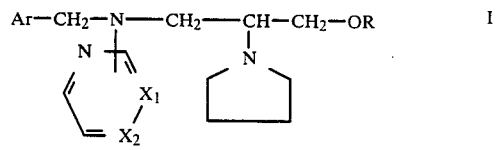

in which
Ar represents thienyl, furyl, pyridyl or an optionally substituted phenyl group,
R represents a linear or branched alkyl group with 1 to 7 carbon atoms, and
either $X_1$ or $X_2$ represents nitrogen, the other being carbon,
and pharmaceutically acceptable acid addition salts thereof, having valuable cardiovascular properties.

8 Claims, No Drawings

3-ALKOXY-2-(N-PYRROLIDINO)-N-PYRIMIDINYL- OR -N-PYRAZINOLPROPYLAMINES USEFUL FOR TREATMENT OF CARDIOVASCULAR DISORDERS

This application is a continuation of U.S. application Ser. No. 688,424, filed Jan. 2, 1985 now abandoned.

The present invention relates to new 3-alkoxy-2-(N-pyrrolidino)-N-pyrimidinyl- or N-pyrazinylpropylamines, to methods for their preparation and to the pharmaceutical composition containing same.

More particularly the compounds correspond to the following general formula:

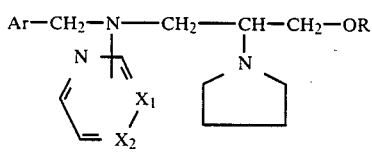

in which
Ar represents thienyl, furyl, pyridyl or an optionally substituted phenyl group,
R represents a linear or branched alkyl group with 1 to 7 carbon atoms, and
either $X_1$ or $X_2$ represents nitrogen, the other being carbon,
and pharmaceutically acceptable acid addition salts thereof.

The compounds of the invention possess valuable cardiovascular properties and more particularly they exert potent anti-anginal, anti-hypertensive and anti-dysrythmic activities.

The compounds of formula I may be prepared by methods known for the preparation of analogous compounds.

The compounds I may be prepared by the reaction of the compound of the formula II:

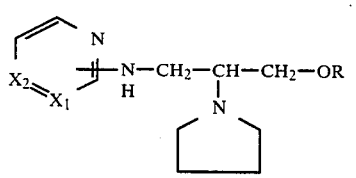

with an amine of the formula III

Ar—CH₂—Hal    III wherein Ar, R, $X_1$ and $X_2$ have the meanings assigned before and Hal represents halogen, and preferably chlorine and bromine.

The starting compound of formula II may, for example, be prepared by a reaction of a compound of the formula IV:

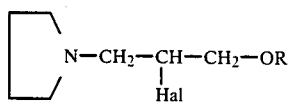

in which Hal and R have the meanings assigned above, with aminopyrimidine or aminopyrazine. This reaction is preferably carried out by first treating the aminopyrimidine or aminopyrazine with an alkalimetal-metallizing agent such as sodiumhydride or sodiumamide.

Another method for the preparation of the compounds of formula I consists of the reaction of a compound of the formula IV with a compound of the formula V:

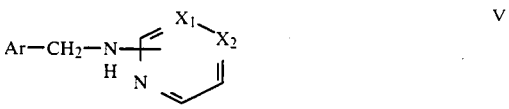

in which Ar, $X_1$ and $X_2$ have the meanings given before.

Preferably this reaction of compound IV with compound V is promoted by first metallizing the latter with an alkalimetal-metallizing agent, such as sodiumhydride or sodium, potassium or lithiumamide.

The compound of formula V may be obtained by a reaction of the aldehyde ArCHO, in which Ar has the meanings mentioned before, with aminopyrimidine or aminopyrazine resulting in an imine, which imine may subsequently be reduced in situ to give the desired secondary amine of formula V. A suitable reducing agent, for example, is sodiumborohydride.

The compounds of general formula I and acid addition salt thereof were shown to possess valuable calcium antagonism properties demonstrated in vitro by usual pharmacological methods, see VAN ROSSUM, Arch. Int. Pharmacodyn. Ther. 143, 299–330 (1963).

In vivo, the anti-anginal activity was investigated by measuring the usual haemodynamic parameters (percentage variation and duration of action) on anaesthetized dogs:

Cardiac frequency with the aid of subcutaneous ECG electrodes.

Coronary arterial output with the aid of an electromagnetic flowmeter.

Anti-tachycardia action (inhibition of the positive chronotropic effects of isoprenaline).

The compounds of the invention are administered intravenously at a dose of 5 mg.kg⁻¹ and the results are reported in Table I.

TABLE I

| Comp. No.* | Cardiac frequency | | Coronary output | | Antitachycardia action | |
|---|---|---|---|---|---|---|
| | Variation (%) | Duration (min.) | Variation (%) | Duration (min.) | Variation (%) | Duration (min.) |
| 1 | −17 | 35 | +252 | 30 | −46 | 30 |
| 3 | −16 | >45 | +32 | 1 | −70 | >45 |
| 4 | −33 | >45 | +150 | >45 | −42 | 30 |
| 5 | −18 | >45 | +86 | 5 | −50 | 30 |
| 6 | −21 | 60 | +196 | 45 | −44 | 30 |
| 7 | −5 | 2 | +67 | 2 | −58 | 5 |

*see table II for the chemical structure of the compounds tested.

The haemodynamic results recorded "in vivo" show that the compounds of the invention have substantialand long-lasting bradycardia and anti-tachycardia activities. Compounds Nos. 1 and 6 are the ones which possess the most substantial coronary dilating activity for a long duration.

The compounds of the invention were also shown to possess a low toxicity; their acute toxicity on oral administration to mice is generally greater than 500 mg.kg⁻¹.

The pharmacological properties therefore make it possible to use the compounds of the invention as drugs for the treatment of cardiovascular disorders such as angina pectoris, hypertension or rhythm disorders.

In association with the usual pharmaceutical excipients, they can be administered enterally or parenterally, preferably by the oral or intravenous route, at daily doses of between 1 and 15 mg per kg of body weight. For the treatment of humans a daily dosage of between 40 and 1200 and more preferably between 100 and 800 mg may be used.

Mixed with suitable auxiliaries the compounds I or salts thereof may be compressed into solid dosage units such as pills, tablets etc., or may be processed into capsules. By means of suitable liquids the compounds may also be applied as an injection- or oral-preparation in the form of solutions, suspensions or emulsions.

The compounds of formula I possess a chiral carbon, as a result of which a racemic mixture I and separate optical enantiomers I are possible. Both the racemic mixture, as well as the separate optical enantiomers belong to the compounds according to the invention. The separate optical enantiomers can be prepared in the usual manner by resolution of the racemic mixture or directly using optically active starting products.

The invention also encompasses the pharmaceutically acceptable acid addition salts of the compounds of formula I. These salts are usually obtained by combining the free base I with inorganic or organic acids such as hydrochloric acid, fumaric acid, maleic acid, citric acid or succinic acid, these acids being mentioned by way of illustration but without implying any limitation.

An optionally substituted phenyl group in the definition of Ar includes an unsubstituted phenyl group and a phenyl group that has been substituted with, for example, halogen, hydroxy, alkoxy (1–4 C) or alkyl (1–4 C). A para-methoxy group is the preferred substituent.

The group

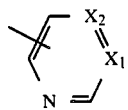

includes the pyrimidinyl and pyrazinyl radicals, whereby the 2-pyrimidinyl radical and the pyrazinyl radicals are to be preferred.

The alkyl group in the definition of R is a linear or branched alkyl group with 1 to 7 carbon atoms, such as methyl, ethyl, propyl, butyl, isobutyl, pentyl, isopentyl and hexyl. The isobutyl radical is the preferred group in the definition of R.

Preferred compounds according to the invention are the compounds of formula I and acid addition salts thereof in which—whether or not in combination:
R represents the isobutyl moiety,
the group

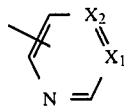

represents a 2-pyrimidinyl or a pyrazinyl moiety and
Ar represents a 2-furyl, a 2-thienyl, a phenyl, a p-methoxy phenyl or a 2-pyridyl radical.

Among the above preferred compounds of formula I those compounds of formula I and acid addition salts thereof, in which the two-nitrogens containing aromatic ring is a 2-pyrimidinyl group and Ar means either the 2-furyl group or the phenyl group or the p-methoxyphenyl group.

EXAMPLE 1

3-isobutoxy-2-(pyrrolidino)-N-pyrazinyl-N-(thien-2-yl-methyl)propylamine 1. 28.5 g (0.3 mol) of aminopyrazine in 400 ml of toluene and 7.5 g (0.25 mol) of 80% sodium hydride were introduced into a 2 liter flask. The mixture was heated under reflux for ½ hour and allowed to return to ambient temperature. Subsequently, 65.9 g (0.3 mol) of 2-chloro-1-isobutoxy-3-pyrrolidinopropane were added and the resulting mixture was refluxed for 18 hours. After the reaction medium had been allowed to return to ambient temperature, it was washed with water, dried over magnesium sulphate and filtered, the solvent was evaporated and the residue was then distilled under reduced pressure.

38 g of 3-(pyrazinyl)amino-2-pyrrolidino-1-isobutoxypropane with a boiling point of 160°–164° C. (at 0.05 mm Hg) was obtained.

2. A mixture of 16.2 g (0.058 mol) of the amine obtained in 1. in 250 ml of toluene and 2.3 g (0.078 mol) of 80% sodium hydride was heated under reflux for 2 hours and allowed to return to ambient temperature. Subsequently 8.5 g (0.064 mol) of 2-chloromethylthiophene were added, after which the mixture was refluxed for 2 hours. After the mixture had been allowed to return to ambient temperature, the excess of sodiumhydride was destroyed with a small quantity of water saturated with NaCl. The mixture was then washed with water, dried over magnesium sulphate and filtered, whereupon the solvent was evaporated and the residue obtained distilled under reduced pressure, yielding 7.7 g of the title product having a boiling point at 0.05 mm Hg of 190°–192° C.

EXAMPLE 2

3-isobutoxy-2-(pyrrolidino)-N-pyrazinyl-N-(4-methoxybenzyl)propylamine

1. A mixture of 300 ml of toluene, 17.5 g (0.184 mol) of aminopyrazine and 31.4 g (0.184 mol) of p-anisaldehyde was heated under azeotropic reflux. After 3 ml of water had been decanted and toluene was evaporated off, the residue was taken up with isopropyl ether and the precipitate obtained was filtered off and dried in vacuo at 30° C. The residue (26.4 g of the imine) was dissolved in 250 ml of methanol after which 5.6 g of NaBH₄ were subsequently introduced in small quantities. The mixture was then left at ambient temperature for 2 hours while stirring. After methanol had been evaporated, the reaction mixture was taken up with 300 ml of ether, whereupon the resulting mixture was washed with water, the organic phase dried over Na₂SO₄ and filtered. Ether was evaporated and the residue was taken up with 100 ml of isopropyl ether. After filtration and recrystallization from absolute ethanol 16.7 g N-4-methoxyphenylmethyl, N-pyrazinyl-amine having a melting point of 105.3° C. were obtained.

2. A mixture of 13.9 g (0.0645 mol) of the above amine, dissolved in 250 ml of toluene and 2.6 g (0.087 mol) of 80% NaH was refluxed for 1 hour 30 minutes. After the mixture had been allowed to return to ambient temperature, 14.2 g (0.0645 mol) of 2-chloro-1-isobutoxy-3-pyrrolidinopropane were added, and the mixture was then heated under reflux for 6 hours. The mixture was then allowed to return to ambient temperature, after which it was hydrolyzed with a small quantity of water, saturated with NaCl, and washed with water. The organic phase was decanted, dried over MgSO$_4$ and filtered. Toluene was evaporated and the residual oil was distilled, retaining the fraction passing over at 200°–202° C. at 0.05 mm Hg.

3. This fraction was dissolved in 100 ml of acetone, and anhydrous hydrogen chloride was bubbled through the solution until the pH was 1. The precipitate was separated and purified yielding 8.5 g of the title compound in the form of the dihydrochloride salt. Melting point: 146.8° C.

EXAMPLE 3

3-isobutoxy-2-(pyrrolidino)-N-(pyrimidin-2-yl)-N-benzylpropylamine

1. A mixture of 19 g (0.020 mol) of 2-aminopyrimidine in 400 ml of toluene, and 7.5 g (0.25 mol) of 80% sodium hydride was refluxed for ½ hour. After the mixture had been allowed to return to ambient temperature, 46.14 g (0.21 mol) of 2-chloro-1-isobutoxy-3-pyrrolidinopropane were introduced all at once and the mixture was heated under reflux for 3 hours. The reaction mixture was cooled down, after which it was washed with water, dried over magnesium sulphate and filtered. The solvent was evaporated and the residue distilled under reduced pressure.

This gave 22 g of 3-isobutoxy-2-(pyrrolidino)-N-(pyrimidin-2-yl)propylamine having a boiling point (at 0.01 mm Hg) of 152°–156° C. and a melting point of: 40.7° C.

2. 14 g (0.046 mol) of the amine obtained in 1. were introduced into 250 ml of toluene, after which 2.2 g (0.073 mol) of sodium hydride were added. The mixture was heated under reflux for 3½ hours. After the mixture had been allowed to return to ambient temperature, 7 g (0.055 mol) of benzyl chloride were added and the mixture was heated under reflux for 1 hour.

After cooling down the reaction mixture, the excess NaH was hydrolyzed and the mixture was washed with water, dried over MgSO$_4$ and filtered. The solvent was evaporated and the residual oil was distilled under reduced pressure.

This gave 5 g of the title product having a boiling point of b.p.$_{0.05}$=167.5° C.

EXAMPLE 4

The following compounds—summarised in Table II—were obtained in a similar manner using the method of Example 1 or the method of Example 2. Table II includes the compounds prepared in the foregoing examples for the sake of completeness. All compounds of Table II have the general formula I, in which R represents the isobutyl radical.

TABLE II

| Compound No. | Ar | 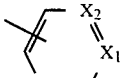 | Salt; melting or boiling point | Prepared according to |
|---|---|---|---|---|
| 1 |  | 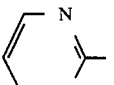 | base b.p.$_{0.05}$: 205° C. fumarate m.p. 98.2° C. | Ex. 1 |
| 2 (Ex. 1) |  | 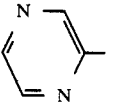 | base b.p.$_{0.05}$ = 191° C. | Ex. 1 |
| 3 |  | 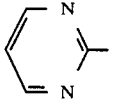 | base b.p.$_{0.1}$ = 171° C. | Ex. 1 |
| 4 |  | 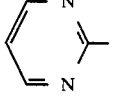 | base b.p.$_{0.05}$ = 220° C. | Ex. 2 |
| 5 (Ex. 2) |  | 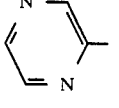 | 2HCl m.p. = 146.8° C. | Ex. 2 |
| 6 (Ex. 3) |  | 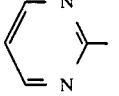 | base b.p.$_{0.05}$ = 167.5° C. | Ex. 3 |

TABLE II-continued

| Compound No. | Ar | 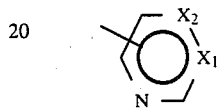 | Salt; melting or boiling point | Prepared according to |
|---|---|---|---|---|
| 7 | phenyl | pyrimidinyl | base b.p.$_{0.05}$ = 183° C. | Ex. 1 |
| 8 | 2-pyridyl | pyrimidinyl | base b.p.$_{0.05}$ = 169° C. | Ex. 1 |

We claim:

1. A compound of the formula:

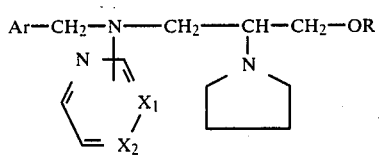

wherein
Ar is thienyl, furyl, pyridyl, phenyl or phenyl substituted by halogen, hydroxy, $C_1$-$C_4$ alkoxy or $C_1$-$C_4$ alkyl,
R is a linear or branched alkyl group with 1 to 7 carbon atoms, and
either $X_1$ or $X_2$ is nitrogen, the other being carbon or a pharmaceutically acceptable acid addition salt thereof.

2. Compound according to claim 1, wherein R represents the isobutyl group.

3. Compound according to claim 1, wherein the group

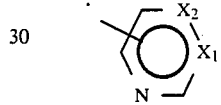

represents the pyrazinyl group.

4. Compound according to claim 1, wherein the group

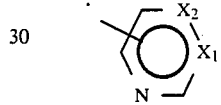

represents the 2-pyrimidinyl group.

5. Compound according to claim 1, in which Ar represents 2-furyl, 2-thienyl, phenyl, p-methoxyphenyl or 2-pyridyl.

6. Compound according to claim 4, in which R represents the isobutyl moiety, and Ar means 2-furyl, phenyl or p-methoxyphenyl.

7. Compound according to claim 6, in which Ar is 2-furyl.

8. A pharmaceutical composition for use in the treatment of cardiovascular disorders, characterized in that it contains, as the active principle, at least one of the compounds according to claim 1 in an effective amount of from 1 to 15 mg/kg of body weight in association with one or more suitable excipients.

* * * * *